United States Patent [19]

Hansen

[11] Patent Number: 4,901,726
[45] Date of Patent: Feb. 20, 1990

[54] RATE-RESPONSIVE, DISTRIBUTED-RATE PACEMAKER

[75] Inventor: James C. Hansen, Denver, Colo.

[73] Assignee: Telectronics N.V., Curacao, Netherlands Antilles

[21] Appl. No.: 355,275

[22] Filed: May 22, 1989

Related U.S. Application Data

[62] Division of Ser. No. 150,037, Jan. 29, 1988, Pat. No. 4,856,522.

[51] Int. Cl.⁴ ............................................. A61N 1/00
[52] U.S. Cl. ............................. 128/419 PG; 128/696
[58] Field of Search ............... 128/420.5, 420.6, 695, 128/696, 702, 703, 731; 237/2 R

[56] References Cited

U.S. PATENT DOCUMENTS 2,889,991  6/1959  Follansbee ........................ 237/2 R
3,940,692  2/1976  Neilson .............................. 128/702
4,403,184  9/1983  Witt et al. .......................... 128/695
4,796,620  1/1989  Imran ................................ 128/702
4,813,417  3/1989  Soli et al. ......................... 128/420.5

Primary Examiner—Francis Jaworski
Assistant Examiner—George Manuel
Attorney, Agent, or Firm—Gottlieb, Rackman & Reisman

[57] ABSTRACT

A rate-responsive heart pacer in which rate-control parameter (RCP) values are arranged in a percentile ranking and mapped onto a percentile ranking of a desired rate distribution. By monitoring the RCP values over an extended time interval and developing a corresponding percentile ranking, the pacemaker automatically self-adapts to long-term changes in RCP measurements and insures that the desired rate distribution is obtained.

6 Claims, 4 Drawing Sheets

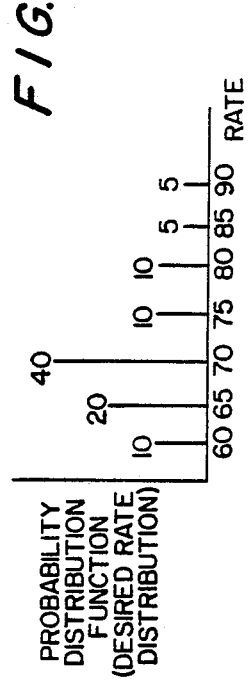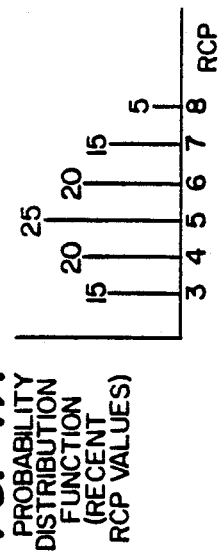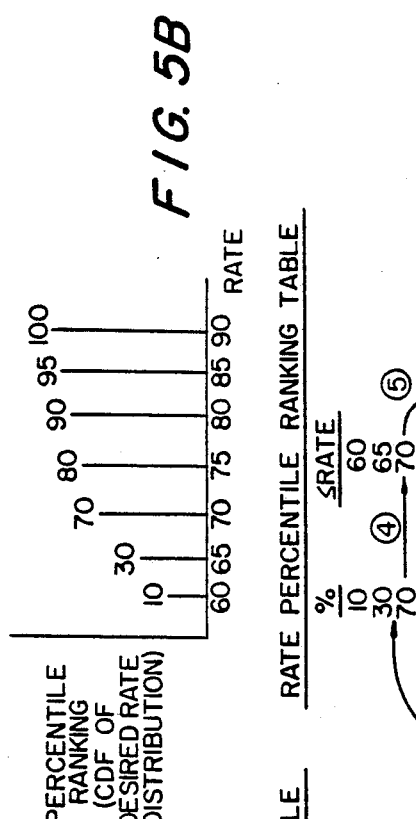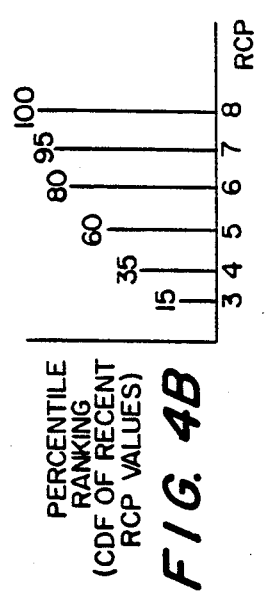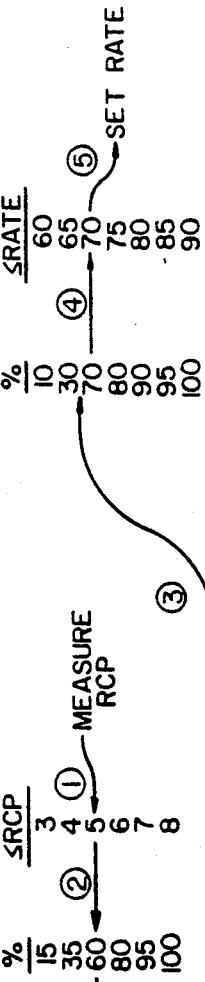
FIG. 4A PROBABILITY DISTRIBUTION FUNCTION (RECENT RCP VALUES)
FIG. 4B PERCENTILE RANKING (CDF OF RECENT RCP VALUES)
FIG. 5A PROBABILITY DISTRIBUTION FUNCTION (DESIRED RATE DISTRIBUTION)
FIG. 5B PERCENTILE RANKING (CDF OF DESIRED RATE DISTRIBUTION)
FIG. 6

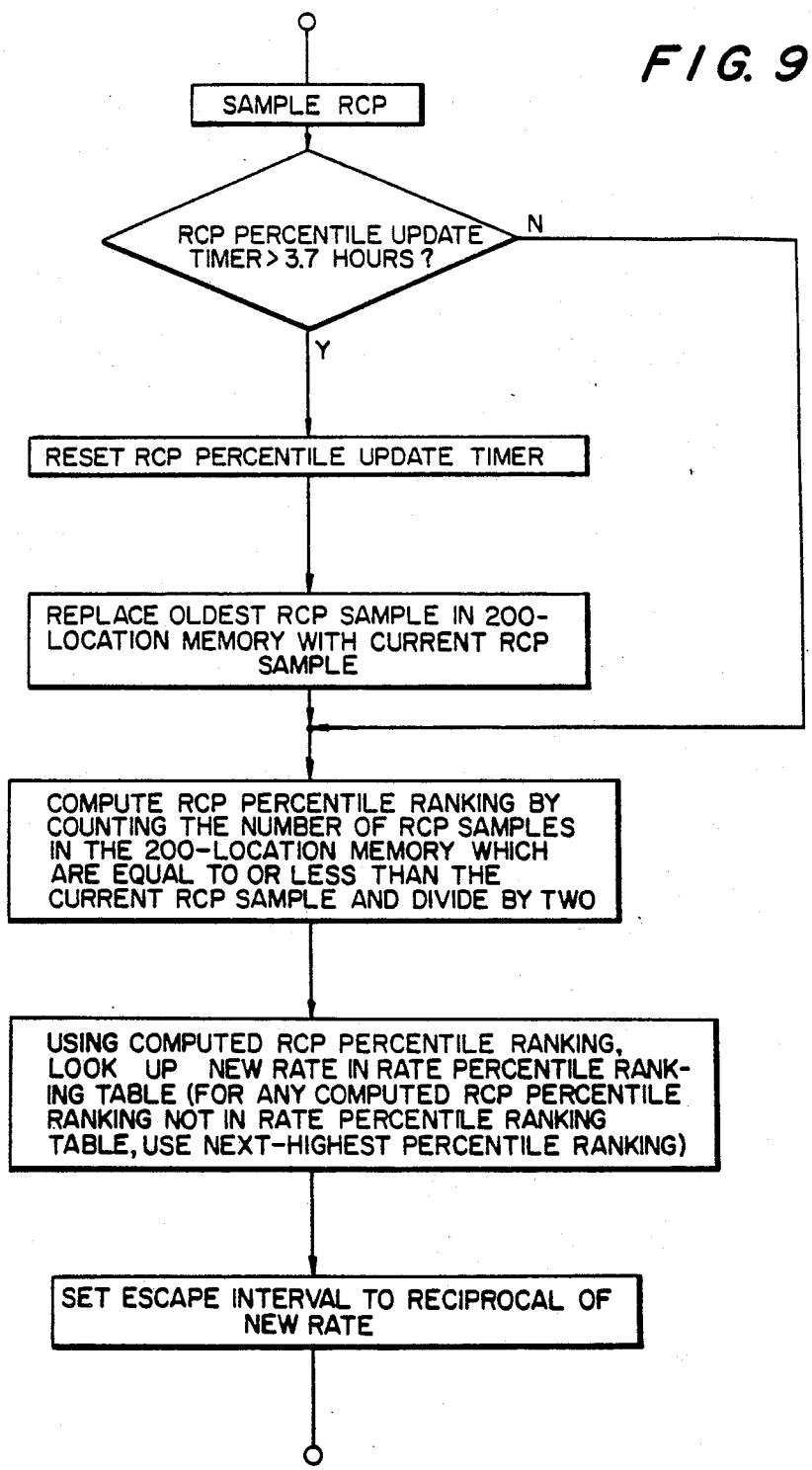

RATE-RESPONSIVE, DISTRIBUTED-RATE PACEMAKER

This is a division of application Ser. No. 150,037, filed Jan. 29, 1988 now U.S. Pat. No. 4,856,522.

This invention relates to rate-responsive pacemakers, and more particularly to a rate-responsive pacemaker which exhibits a predetermined rate distribution independent of the distribution of the rate-control parameter.

A rate-responsive pacemaker is one which adjusts its rate in accordance with the value of a measured parameter. Because the value of the parameter is used to control the rate, it is generally referred to as a rate-control parameter (RCP). The RCP varies with the physiological needs of the body and is dependent upon such factors as stress, and whether the patient is exercising or at rest. Illustrative rate-control parameters include respiratory minute volume, QT interval, temperature and physical vibration. A rate-responsive pacemaker generally exhibits some characteristic which expresses the desired rate as a function of the RCP. Where the rate control is based upon such a built-in characteristic, there are necessarily several disadvantages.

One of the disadvantages is that the RCP value for any given state of stress or exercise does not remain constant for the life of the pacemaker. In some cases the RCP is measured by a sensor attached to a pacemaker lead, or it is derived from the sensed electrogram signal. In either case, if the lead changes position, all values of the RCP may be shifted. If there is no way to account for shifts of this kind, it is possible for all pacing rates to be shifted downwardly or upwardly.

Another shortcoming of most rate-responsive pacemakers is that they entail complex set-up procedures. (See, for example, Application Serial No. 150,038, filed on Jan. 29, 1988 in the name of Nappholz et al and entitled "Minute Volume Rate-Responsive Pacemaker".) There are other disadvantages with present-day approaches to rate-responsive pacing, and they will become apparent when the advantages of the subject invention are described below.

It is a general object of my invention to provide a rate-responsive pacemaker which overcomes the disadvantages of the general prior art approach in which there is a one-to-one correspondence between pacing rate and RCP value. (The invention has more general applicability in that it can be used in any automatic gain control system for relating a controlled parameter to a controlling parameter.)

In accordance with the principles of my invention, the pacemaker is not programmed to pace at a particular rate for a particular value of the RCP. Instead, there is stored a function which represents the desired rate distribution. Using discrete values, the function might call for a rate of 70 beats per minute (bpm) to be the operative rate 40% of the time, a rate of 80 bpm to be the operative rate for 10% of the time, etc. The pacemaker also generates a probability distribution function of recent RCP values. For example, it may be determined that over the last month or so 25% of the time the RCP had a value of 5, 20% of the time it had a value of 6, etc. From these two functions, two percentile rankings are developed. Each percentile ranking is a cumulative distribution function. The function for the desired rate distribution might represent that the rate should be less than 60 bpm 10% of the time, less than 65 bpm 30% of the time, less than 70 bpm 70% of the time, etc. The percentile ranking for the recent RCP values takes a similar form. For example, the RCP values over the last month may have been less than 3 15% of the time, less than 4 35% of the time, less than 5 60% of the time, etc.

The two percentile rankings are then used to determine the pacing rate at any instant. The instantaneous RCP is measured and its percentile ranking is determined from the percentile ranking table of recent RCP values. Using that percentile, the percentile ranking table for rates is consulted. The rate corresponding to the previously determined percentile is the one used by the pacemaker.

The net result is that the rates at which the pacemaker paces have a probability distribution which corresponds to the desired (programmed) rate distribution. The pacemaker is self-adapting, provided that there is maintained a probability distribution function for recent RCP values. As the RCP values change with the administration of drugs and other long-term effects, the rate distribution is automatically mapped onto the RCP value distribution.

Further objects, features and advantages of my invention will become apparent upon consideration of the following detailed description in conjunction with the drawing, in which:

FIGS. 4A and 4B depict a typical RCP probability distribution function (histogram) and corresponding percentile ranking in the illustrative embodiment of the invention;

FIGS. 5A and 5B depict a typical desired rate probability distribution function and percentile ranking in the illustrative embodiment of the invention;

FIG. 6 depicts the percentile rankings of FIGS. 4B and 5B in table form, and further illustrates the steps involved in going from a measured RCP value to the setting of the pacing rate;

FIG. 9 is a flow chart of the steps executed in the "Sample RCP and Update" block of FIG. 8.

Figures 1, 2, 3, 7:
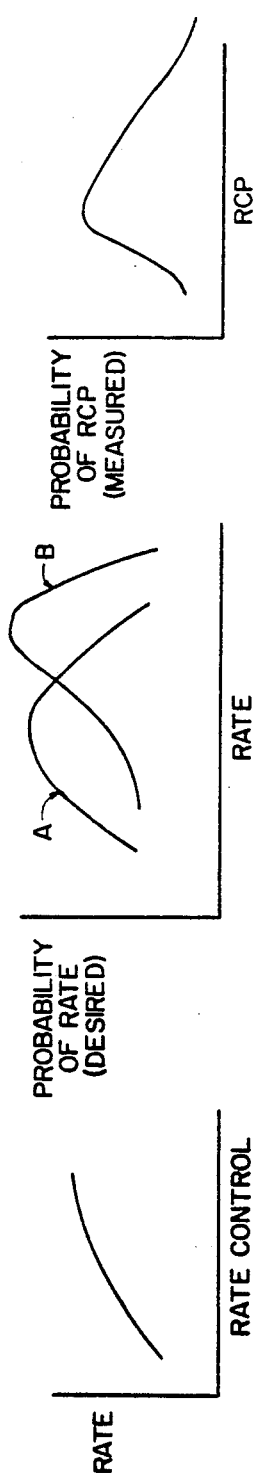
FIG. 1 depicts the general prior art approach by which the rate of a rate-responsive pacemaker is determined from the value of an RCP.
FIG. 2 represents two examples of a rate distribution which may be desired by a physician.
FIG. 3 depicts a typical probability function for measured RCP values.
FIG. 7 is a block diagram of a pacemaker which implements the method of my invention.

The curve of FIG. 1 is the kind of function which characterizes a typical prior art rate-responsive pacemaker. For every value of the rate-control parameter, there is a corresponding pacing rate. The characteristic may be non-linear not only because the sensor itself may be a non-linear device, but also because it may be desired that the pacing rate vary with RCP in a non-linear fashion. The basic problem with providing a pacemaker with a built-in function of the type represented by FIG. 1 is that the function must change with time if the same level of stress is always to result in the same pacing rate. This is because RCP values typically vary with the administration of drugs, changes in sensor sensitivity over time, etc.

The basis for the present invention is that there is a desired probability distribution of pacing rates, of the type depicted in FIG. 2. A physician might desire that curve A characterize the pacer operation. What the curve represents is the probability of occurrence of every pacing rate. The probability function is comparable to the probability distribution function of FIG. 5A, the latter representing a distribution in terms of discrete rates. Referring to FIG. 5A, it is assumed that the physician desires that there be only seven possible rates, ranging from 60 to 90 bpm, in 5-bpm increments. The desired rate distribution is such that a rate of 60 bpm will apply 10% of the time, a rate of 65 bpm will apply 20% of the time, etc. Curves A and B of FIG. 2 represent the same kind of thing, except they take into account all rates and the vertical axis represents probability (with the area under each curve being equal to unity). In the illustrative embodiment of the invention continuous curves of the type shown in FIG. 2 do not play a part. However, they are helpful in understanding the invention from a conceptual standpoint. The physician programs the pacemaker with values such as those represented in FIG. 5A—a probability distribution function for seven specific rates. It should be noted that the seven probability values add up to 100% since it is assumed that only seven discrete values of rate are permitted. Two curves are shown in FIG. 2 in order that it be appreciated that the physician may program different probability distribution functions into a pacemaker. Curve A might apply to an inactive patient, while curve B might apply to an active patient; in the latter case, the rate curve is skewed toward a higher range. In general, it is contemplated that there might be three probability distribution functions which the physician might choose from in programming the pacemaker, for sedate, normal and active patients. One such probability distribution function is shown in FIG. 5A. Whichever function is programmed, that is the function which the physician desires to apply to the patient for the life of the pacemaker, or at least until it is re-programmed.

It should be noted that the probability distribution function in no way correlates rates and RCP values. All that is known from the probability distribution function is that if a continuous record is kept of how often the pacer operated at each of the possible rates, it will be found that each rate was in effect for a percentage of the total time which corresponds to that shown in FIG. 5A. How the desired distribution is achieved based upon measured values of RCP is what the invention is all about.

Whereas FIG. 2 depicts the desired probability of rate, the curve of FIG. 3 depicts the probability of RCP values as actually measured. For each value of RCP, there is a certain probability that it will be measured. The curve of FIG. 3 is not fixed as is the desired rate probability occurring depends upon long-term changes, drug therapies, changes in sensor sensitivity, changes in patient lifestyle, etc. In other words, a curve such as that shown in FIG. 3 represents the actual measurements of RCP, whereas curve A or curve B of FIG. 2 represents a permanent desired rate distribution.

FIG. 4A represents a probability distribution function of recent RCP values. In accordance with the principles of the invention, running counts are maintained of measured RCP values. Only discrete values of RCP are considered; thus an RCP value such as 4.7 would be treated as a value of 5. The probability distribution function values are shown in FIG. 4A in normalized fashion, that is, each value is a percentage with the total adding up to 100%. What this means, for example, is that of all possible RCP values over the last month or so, a value of 5 was measured 25% of the time, a value of 6 was measured 20% of the time, etc. FIGS. 4A and 5A are comparable in that they are both normalized so that the individual probabilities in each case add up to 100%.

While the probability distribution function of FIG. 4A was said to be based on values measured over the last month, it is to be understood that the precise interval is not important. What is important is that the pacer have available some kind of record which shows how the RCP measurements are varying on a long-term basis. The question is how to relate a probability distribution function of RCP values to a probability distribution function of desired rates, i.e., how to go from an instantaneously measured value of RCP to an instantaneous rate to be used based upon the two probability distribution functions.

The first step in relating RCP values to rate is to recast the probability distribution functions of FIGS. 4A and 5A into percentile rankings of RCP values and rates, as shown in FIGS. 4B and 5B. A percentile ranking is the same as a cumulative distribution function (CDF). Consider the RCP value of 5 in the probability distribution function of FIG. 4A. A value of 5 is measured 25% of the time, as shown in the figure. Similarly, a value of 3 is measured 15% of the time and a value of 4 is measured 20% of the time. What this means is that values of 3, 4 or 5 are measured 60% of the time. That is the way in which a percentile ranking of 60 is developed for an RCP value of 5 in FIG. 4B. The percentile ranking of the highest possible RCP, a value of 8, is necessarily 100 because all measured RCP values are less than or equal to 8. A percentile ranking is necessarily a monotonically increasing function. In a similar manner the percentile ranking of the desired rates can be derived from the corresponding probability distribution function, although the percentile ranking can actually be programmed in the pacer without having to go through the mathematical manipulation starting with a probability distribution function of rates. Referring to FIGS. 5A and 5B, for example, rates of 75 bpm or less occur 80% of the time (as shown in FIG. 5B), and this value is derived by adding together the four individual probabilities (10%, 20%, 40% and 10%) for the four rates which are equal to 75 bpm or less in FIG. 5A.

Given the percentile rankings of RCP and rate, one is mapped onto the other in accordance with the principles of my invention. Both are monotonically increasing functions and it is relatively simple to determine the rate which should apply for any measured value of RCP—even though the overall range of RCP values, and the probability distribution within that range, vary with time. The steps involved are shown in FIG. 6. Two tables are included in the drawing. The table on the left is derived from the percentile ranking of FIG. 4B, and the table on the right is derived from the percentile ranking of FIG. 5B. For example, referring to FIG. 4B it will be seen that RCP values equal to or less than 6 have been measured (over the last month or so) 80% of the time. That is why the percentage column in the RCP percentile ranking table includes a value of 80 for an RCP value of 6 or less. Both tables are simply another way of representing the percentile rankings of FIGS. 4B and 5B.

The rate which is set in the pacemaker is derived in the following way, with reference to a particular example. In the following discussion, the steps of the method are shown by the circled digits 1–5. The first step involves measuring the instantaneous value of the RCP, something which is done in every rate-responsive pacemaker. [As mentioned above, the particular RCP is of no moment insofar as the subject invention is concerned, although the assignee of this application markets a rate-responsive pacemaker in which the RCP is respiratory minute volume.]It is assumed in the example that the measured value of RCP is 5. In the case illustrated, all RCP values are to the nearest integer, and all rate values are to the nearest multiple of 5 bpm. The RCP percentile ranking table is consulted and in step 2 it is determined that the pacemaker has been operating over the last month or so such that values of RCP of 5 or less have been measured 60% of the time.

In the third step, this percentile value of 60 is used as an entry into the rate percentile ranking table. There is no percentile value of 60 since the values derived from FIG. 5B in the illustrated example have a table entry of 70 following a table entry of 30. The next highest table entry is selected, 70 in this case. It is known from the rate percentile ranking table that a rate equal to or less than 70 bpm is desired 70% of the time. In the last step, the pacer is set to operate at a rate of 70 bpm.

It is in step 3 that the correspondence is established between the RCP percentile ranking and the desired rate percentile ranking. It is not possible to relate to selves. Referring to FIG. 4A, it will be seen that RCP values of 4 and 6 both occur 20% of the time. Referring to FIG. 5A, a rate of 65 is desired by the physician to apply 20% of the time. Since any rate versus RCP curve such as that shown in FIG. 1 is generally monotonically increasing as shown, or decreasing, it would not be possible to relate only one of the RCP values of 4 and 6 to the 65-bpm rate. This is not to say that with monotonically increasing or decreasing functions several values of RCP will not map onto the same rate. For example, referring to FIG. 6 it will be seen that RCP values of both 4 and 5 map to a rate of 70 bpm. (The percentile ranking for an RCP of 4 is 35%, this rate percentile ranking table of FIG. 6, and consequently in the fourth step a rate of 70 bpm is once again selected ) But this is simply a matter of quantization. Referring to FIG. 5A it will be seen that rates of 65 and 70 bpm are desired a total of 60% of the time. It is therefore to be expected that multiple values of RCP will map onto the 65–70 bpm region of the rate percentile table. If the probability distribution function of desired rate involves smaller discrete steps, then there will be fewer "big jumps". It is apparent, for example, that because a rate of 70 bpm is to occur 40% of the time, there necessarily has to be a 40% jump in the rate percentile ranking table as shown in FIG. 6. Obviously the jumps would be much smaller if rates of 67, 69, 71 and 73 were each to occur 10% of the time.

One question is why in step 3 of FIG. 6 an entry is made to the percentile ranking of 70 rather than a percentile ranking of 30. It is not because the value of 60 taken from the RCP percentile ranking table is closer to 70 than to 30. Were the RCP value measured equal to 4 and a percentile ranking of 35 derived from the left table of FIG. 6 in step 2, the entry to the rate percentile ranking table would still be to the 70 line rather than the 30 line, even though 35 is closer to 30 than to 70. The reason has to do with the mapping rationale. In the example shown in FIG. 6, an RCP value exists such that this value and lesser values have been obtained 60% of the time over some relatively long interval. What is therefore desired is a rate such that that rate and slower rates similarly are desired 60% of the time. Were the rate percentile ranking table of FIG. 6 entered at the 30 level, for which a rate of 65 bpm would be set, what it would mean is that a rate was selected such that that rate and lower values are desired 30% of the time. That does not correspond to RCP values which have been measured 60% of the time. But an entry to the rate percentile ranking table at the 70 line means that the rate which will be set and all lower rates are desired 70% of the time. This necessarily means that they are desired at least 60% of the time, and this corresponds to the range of RCP values (3–5) which have been measured 60% of the time.

Referring to FIG. 6, it will be seen that for a measured RCP value of 3, the percentile ranking is 15. In step 3 of the method of the invention, the rate percentile ranking table is entered between the 10 and 30 percentiles, and this means that the 30 line is selected, i.e., the lowest rate which can be set is 65 bpm even though the physician included a 60-bpm rate in his rate distribution. With finer quantization, however, it is likely that such a situation will not arise. Furthermore, it is certainly possible that in the future RCP values of 3 or less will be represented less than 15% of the time. For example, suppose that they exist only 8% of the time. In such a case, the first entry in the RCP percentile ranking table will be less than 8, and for any value of RCP of 3 or less a rate of 60 bpm will be selected from the rate percentile ranking table.

The block diagram of FIG. 7 depicts the manner in which a pacemaker can be constructed to implement the subject invention. A sensor input is applied over line 8 to RCP sampler 10. The sensor input may be a chemical measurement, an electrical parameter or even the signal picked up by a pacemaker electrode (shown by the numeral 35). The RCP sampler 10 simply delivers periodic samples of the RCP to microprocessor 15. The microprocessor cooperates with memory 20 to derive its operating instructions and for storing data. The microprocessor senses cardiac potentials amplified by amplifier 30, and similarly causes pulse generator 25 to generate a pacing stimulus when it is needed.

Figure 8:
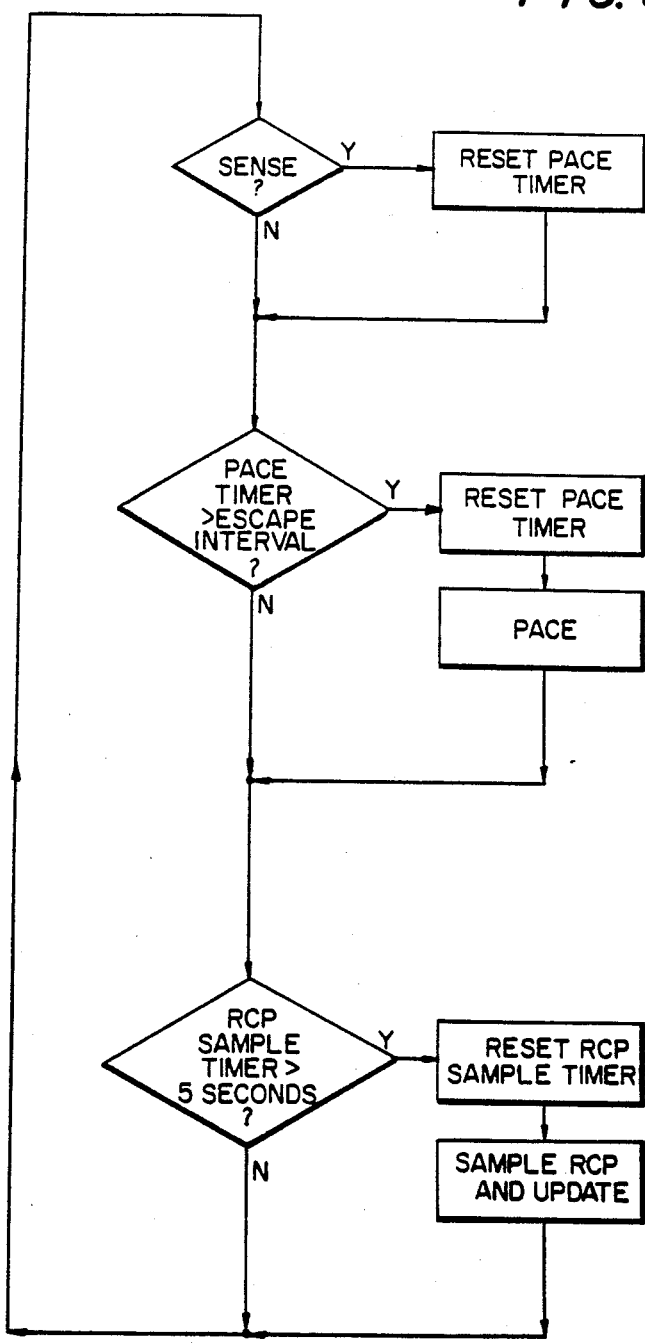
FIG. 8 is a flow chart of the master processing loop of the pacemaker of FIG. 7.

The illustrative embodiment of the invention is a VVI pacer; it can be standard in all respects except that its escape interval is adjusted in accordance with the current value of the RCP. The master processing loop flow chart is shown in FIG. 8. At the top, a test for heartbeat sensing is shown. If a heartbeat is sensed, the pace timer is reset so that a new escape interval can be timed. However, if a heartbeat is not sensed, a check is made whether the time which has elapsed since the last resetting of the timer is greater than the escape interval. If it is, it is an indication that a stimulus is required, and two steps now take place. First, the pace timer is reset so that another cycle of operation can begin. Second, the patient is paced by causing pulse generator 25 on FIG. 7 to operate.

Next in the flow chart is a test whether the RCP sample timer exceeds five seconds. In the illustrative embodiment of the invention, RCP samples are taken every five seconds. As long as five seconds have not elapsed since the last sample was taken, the system simply moves on to the sense step at the top of the flow chart. But if five seconds have gone by, the first thing that is done is to reset the RCP sample timer in preparation for another cycle. An RCP sample is then taken and various updating operations take place. The box labeled "sample RCP and update" on the flow chart of FIG. 8 is shown in detail in FIG. 9; it is in the flow chart of FIG. 9 that the various steps described with reference to FIGS. 4–6 are carried out.

After an RCP sample is taken, as shown at the top of FIG. 9, a check is made whether the RCP percentile update timer exceeds 3.7 hours. In the illustrative embodiment of the invention, the percentile ranking of FIG. 4B is updated approximately six times per day. The timer is not exactly four hours because that would mean that six samples would be taken every day, at the same six times every day. By taking slightly more than six samples in every 24-hour period, the sample values which are stored are more representative of all RCP values, with each time of day being given equal importance.

If it is time for the percentile ranking of FIG. 4B to be updated, the RCP percentile update timer is reset so that another sample will be used to update the ranking 3.7 hours from now. Then the oldest RCP sample in a 200-location memory is replaced with the current sample. The system stores the most recent 200 samples. If approximately six samples are taken each day, the samples stored represent the RCP values measured during the last month of pacer operation.

Once the current sample replaces the oldest sample in the 200-location memory, the new percentile ranking is computed. How this is done is described in the next step on FIG. 9. Although the probability distribution function of FIG. 4A need not actually be derived, and instead the percentile ranking of FIG. 4B can be derived directly from the 200 stored samples, it is convenient to consider the processing in two steps. First, as shown in FIG. 4A, a count is taken of the samples which correspond to each discrete value of RCP for which a count is maintained; the total is divided by two to derive the probability distribution function value for that particular RCP. The percentile ranking of FIG. 4B for each value of RCP is then computed simply by adding together the probability of that value of RCP and the probabilities of all RCPs of lesser value. In effect, the percentile ranking which is derived represents the history of RCP measurements over the last month or so.

The next step in FIG. 9 describes what is shown in FIG. 6 of the drawing. It should be appreciated that although RCP samples are used to update the percentile ranking only approximately once every four hours, an RCP sample is taken every five seconds, as shown in FIG. 8, and every five seconds the pacing rate is adjusted in accordance with the steps shown in FIG. 6. The last step in the flow chart of FIG. 9 simply entails setting the escape interval so that it is equal to the reciprocal of the new rate; as is known in the art, the escape interval is simply the reciprocal of the rate.

With this description in mind, there are several advantages of the invention which are noteworthy. The first relates to the concern which has existed since the early days of pacemakers about the generation of pacing pulses at rates which are excessively high. While a pacemaker usually includes a rate limiting circuit so that a maximum rate cannot be exceeded, that does not necessarily prevent sustained pacing at the maximum rate. In the invention, however, no matter how "wild" the RCP values become, high pacing rates cannot be sustained. In effect there is a form of negative feedback; the pacer self-adapts to the RCP value distribution, even if all of the values are unusually high.

Another advantage relates to the fact that if a typical prior art rate-responsive pacemaker is not set up properly for a particular patient, the rate-responsive capability of the device will generally be useless. In the invention, however, not only is improper set-up of little concern, but there may be no need for set-up at all. Whatever the RCP values happen to be, and even if they are way too high or way too low because of improper set-up, the RCP percentile ranking is automatically mapped onto the percentile ranking of the desired rate distribution. The set-up procedure described in the above-identified Nappholz et al application requires measurements to be taken of the RCP while the patient is at rest and, after an interval of about an hour, when he suddenly starts to exercise strenuously. The RCP values are telemetered from the pacer and used by the programmer to program the pacer. In the invention there is no need for all of this, as the pacer self-adapts to long-term changes in RCP measurements which do not relate to instantaneous physiological needs.

Another advantage pertains to the fact that prior art rate-responsive pacemakers pace at the nominal rate most of the time, with the rate going up when the patient is subject to stress or when he exercises. But there is often no difference in rate when the patient is sitting in a chair and when he is sleeping. If the set-up procedure involves a measurement of the RCP which corresponds to the minimum rate when the patient is at rest, there is generally no way to decrease the rate when the patient is sleeping. To do that would require that the minimum rate be set so that it corresponds to a still lower value of RCP which might be measured while the patient is asleep. (Throughout this discussion it is assumed that increasing values of RCP correspond to increasing rates; obviously, the same remarks still apply if in a particular case an inverse relationship exists.) It might be possible to extrapolate, that is, to measure the RCP value of a patient at rest and to compute what it should be when he is asleep so that the computed value could be set to correspond to the minimum rate. However, extrapolations of this type are usually not accurate. In the invention, on the other hand, the RCP values which are stored include those taken while the patient is sleeping. Those values go to make up the percentile ranking just as do the other values, and thus those values also map onto the desired rate distribution. Consequently, it is possible to provide true rate-responsive pacing over the entire gamut of patient activity.

A most significant advantage of the invention is that it is applicable to any rate control parameter. There is no need for different kinds of processing depending on the particular RCP which is used. The entire product line of a manufacturer may provide the same kind of operation, whether the individual pacemakers use rate control parameters involving temperature, minute volume, stroke volume, etc. The RCP values are completely arbitrary in the sense that there is no predesigned correspondence between them and the desired rates. The RCP can even be a non-linear parameter without affecting the self-adaptation (as long as changes in the RCP are monotonic). Even if the sensor is not working properly, whatever values of RCP actually exist have their percentile ranking automatically mapped onto the percentile ranking of the desired rate distribution. This is a remarkable result. What it means is that if a sensor or the circuitry for processing the measured RCP signal suddenly changes characteristics, that does not mean that the pacemaker no longer functions properly. It may take a month or so for the new percentile ranking of RCP values to be mapped onto the percentile ranking of the desired rate distribution, but once that takes place the pacemaker will operate as it did before. One obvious advantage of this is that the RCP processing may be made logarithmic so that the sensitivity at low values may be increased.

In essence, the rate-responsive pacemaker of the invention exhibits a predetermined rate distribution, regardless of the distribution of the rate-control parameter values. This does not mean that the pacemaker ignores the parameter. On the contrary, the invention is a method of transforming an arbitrarily distributed parameter into a rate with a predetermined distribution. Two properties characterize the pacer of the invention. First, it is guaranteed to exhibit a programmed rate distribution. Second, the pacing rate is guaranteed to change monotonically with the measured RCP value so that as the RCP changes in any given direction, the pacing rate always changes in a corresponding direction.

Although the invention has been described with reference to a particular embodiment, it is to be understood that this embodiment is merely illustrative of the application of the principles of the invention. For example, instead of the percentile ranking of RCP values being based upon values measured over the course of a month, they could be taken over a week and perhaps over as short an interval as one day. Also, in those cases where the RCP is not monotonic in nature, it can be transformed into a monotonic parameter suitable for use in the invention. It is known, for example, that blood temperature dips at the onset of demand, but then increases. An RCP based on temperature might be transformed to a new parameter which increases in response to a sudden dip and also increases in response to an increase in temperature. In such a case it would be the transformed parameter which would be treated as the RCP whose values are ranked. Thus it is to be understood that numerous modifications may be made in the illustrative embodiment of the invention and other arrangements may be devised without departing from the spirit and scope of the invention.

I claim:

1. A control system comprising means for measuring a value of a controlling parameter; means for adjusting a controlled parameter; and control means for (a) calculating a total percentage of time, over an interval which is much longer than the response time of the system, that said controlling parameter is equal to or less than each of at least several values, (b) for representing a desired controlled-parameter distribution which for each of different percentages of time indicates said controlled parameter equal to or greater than that which is desired, and (c) responsive to a measured value of said controlling parameter, for relating said calculated total percentage of time for that controlling parameter to said desired controlled parameter for that percentage of time and for causing said adjusting means to adjust said controlled parameter to equal said desired controlled parameter for that percentage of time.

2. A method for operating a control system comprising the steps of measuring a value of a controlling parameter; calculating a total percentage of time, over an interval which is much longer than the response time of the system, that said controlling parameter is equal to or less than each of at least several values; representing a desired controlled-parameter distribution which for each of different percentages of time indicates a controlled parameter equal to or greater than that which is desired; and relating said calculated total percentage of time for a measured value of said controlling parameter to said desired controlled parameter for that percentage of time and adjusting said controlled parameter to equal said desired controlled parameter for that percentage of time.

3. A method for operating a control system comprising the steps of periodically measuring a value of a controlling parameter, calculating a first function which represents a distribution of different controlling-parameter values over a time interval which is substantially greater than the response time of the controls system, storing a second function which represents a desired distribution of a controlled parameter, and relating said first and second functions to determine the instantaneous controlled parameter applicable to a measured controlling-parameter value.

4. A method in accordance with claim 3 wherein said first function is a percentile ranking of controlling-parameter values, and said second function is a percentile ranking of desired controlled parameter values.

5. A method in accordance with claim 4 wherein said applicable controlled parameter is determined by ascertaining from said first function the percentile rank for a measured controlling-parameter value, and using a corresponding percentile rank to ascertain the controlled parameter from said second function.

6. A method in accordance with claim 5 wherein said corresponding percentile rank is the one ascertained from said first function or, if not present in the percentile ranking of said second function, then the next highest percentile rank in said second function.

* * * * *